United States Patent [19]

Ueda et al.

[11] Patent Number: 4,703,046

[45] Date of Patent: * Oct. 27, 1987

[54] CEPHEM COMPOUNDS AND PROCESSES FOR PREPARATION THEREOF

[75] Inventors: Ikuo Ueda, Toyonaka; Masakazu Kobayashi, Ikeda; Tadashi Kitaguchi, Kukuchinishi, all of Japan

[73] Assignee: Fujisawa Pharmaceutical Co., Ltd., Osaka, Japan

[*] Notice: The portion of the term of this patent subsequent to Jan. 24, 2001 has been disclaimed.

[21] Appl. No.: 72,990

[22] Filed: Sep. 6, 1979

[30] Foreign Application Priority Data

Sep. 8, 1978 [GB] United Kingdom ............... 36131/78

[51] Int. Cl.$^4$ .................. A61K 31/545; C07D 501/20
[52] U.S. Cl. ....................................... 514/202; 540/222
[58] Field of Search ............. 544/27, 22, 28; 424/246; 514/200, 203, 206, 202; 540/222

[56] References Cited

U.S. PATENT DOCUMENTS

| | | | |
|---|---|---|---|
| 4,008,246 | 2/1977 | Ochiai | 544/22 |
| 4,098,888 | 7/1978 | Ochiai et al. | 544/27 |
| 4,152,433 | 5/1979 | Kamiya et al. | 544/22 |
| 4,203,899 | 5/1980 | Ochiai | 544/22 |
| 4,254,119 | 3/1981 | Hamashima et al. | 544/22 |
| 4,279,818 | 4/1981 | Takaya | 544/22 |
| 4,293,550 | 10/1981 | Blumbach et al. | 544/28 |
| 4,298,606 | 11/1981 | Ochiai et al. | 544/21 |
| 4,425,341 | 1/1984 | Takaya | 544/16 |
| 4,427,674 | 1/1984 | Takaya | 544/16 |
| 4,438,113 | 5/1984 | Takaya | 544/22 |
| 4,460,583 | 7/1984 | Takaya | 544/22 |
| 4,463,002 | 4/1984 | Takaya | 544/22 |
| 4,470,983 | 9/1984 | Blumbach | 544/22 |
| 4,477,447 | 10/1984 | Ueda | 544/22 |
| 4,489,072 | 12/1984 | Sadaki | 544/22 |
| 4,496,562 | 1/1985 | Takaya | 544/22 |

FOREIGN PATENT DOCUMENTS 0002765 7/1979 European Pat. Off. .

*Primary Examiner*—Esther M. Kepplinger
*Assistant Examiner*—Robert Benson
*Attorney, Agent, or Firm*—Oblon, Fisher, Spivak, McClelland, & Maier

[57] ABSTRACT

This invention concerns antibiotic cephalosporins of the formula

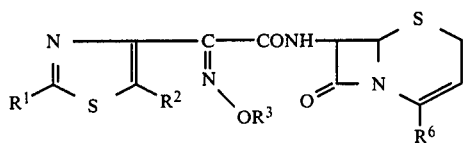

wherein $R^1$ is amino or protected amino; $R^2$ is halogen; $R^3$ is alkyl; and $R^6$ is carboxy or protected carboxy.

12 Claims, No Drawings

CEPHEM COMPOUNDS AND PROCESSES FOR PREPARATION THEREOF

This invention relates to new cephem compound. More particularly, it relates to new 7-substituted-3-cephem-4-carboxylic acid, its pharmaceutically acceptable salt and pharmaceutically acceptable bioprecursor thereof, which have antimicrobial activities, and processes for preparation thereof, to intermediate for preparing the same and processes for preparation thereof, and to pharmaceutical composition comprising the same and methods of using the same prophylactically and therapeutically for treatment of infectious diseases in human being and animals.

Accordingly, the objects of this invention are to provide:

new 7-substituted-3-cephem-4-carboxylic acid, its pharmaceutically acceptable salt and pharmaceutically acceptable bioprecursor thereof, which exhibit excellent antimicrobial activities against a wide variety of pathogenic microorganisms including Gram negative and Gram positive bacteria, processes for preparation of the same, pharmaceutical composition comprising one of the same as an active ingredient, and a method of using the same prophylactically and therapeutically for treatment of infectious diseases caused by pathogenic microorganisms in human being and animals; and further intermediate to be used for preparation of pharmaceutically active 7-substituted-3-cephem-4-carboxylic acid, its pharmaceutically acceptable salt or pharmaceutically acceptable bioprecursor thereof, and method for preparation of the same.

The cephem compounds of this invention can be represented by the formula (I):

$$\text{(I)}$$

wherein
$R^1$ is amino or protected amino,
$R^2$ is halogen, lower alkyl, lower alkoxy or lower alkylthio,
$R^3$ is hydrogen or lower alkyl,
$R^4$ is hydrogen, lower alkyl or lower alkoxy,
$R^5$ is hydrogen, halogen, lower alkyl, lower alkoxy, hydroxymethyl, acyloxymethyl or heterocyclic-thiomethyl in which the heterocyclic moiety may be substituted with lower alkyl or lower alkenyl, and
$R^6$ is carboxy or functionally modified carboxy, and its pharmaceutically acceptable salt and a pharmaceutically acceptable bioprecursor thereof.

The terms and definitions described in this specification are illustrated as follows.

(a) Partial structure of the formula:

$$-\underset{\underset{\underset{O-R^3}{|}}{N}}{\overset{\|}{C}}-CO-$$

is intended to mean both of the geometric formulae:

$$\underset{(S)}{-\underset{N-O-R^3}{\overset{\|}{C}}-CO-} \quad \text{and} \quad \underset{(A)}{-\underset{R^3-O-N}{\overset{\|}{C}}-CO-}$$

The geometry of the formula (S) is referred to as "syn" and another formula (A) is referred to as "anti". Accordingly, one isomer having the partial structure of the above formula (S) is referred to as "syn isomer" and another isomer having the alternative one of the above formula (A) is referred to as "anti isomer", respectively.

From the view point of structure-activity relationship, it is to be noted that a syn isomer of the compound (I) tends to be of much higher antimicrobial activity than the corresponding anti isomer, and accordingly the syn isomer of the compound (I) is more preferable antimicrobial agent than the corresponding anti isomer in the prophylactic and therapeutic value.

(b) The thiazolyl group of the formula:

(wherein $R^1$ and $R^2$ are each as defined above) is well known to lie in tautomeric relation with a thiazolinyl group of the formula:

(wherein $R^{1'}$ is imino or protected imino).

The tautomerism between the said thiazolyl and thiazolinyl groups can be illustrated by the following equilibrium:

(wherein $R^1$ and $R^{1'}$ are each as defined above).

Accordingly, it is to be understood that both of the said groups are substantially the same, and the tautomers consisting of such groups are regarded as the same compounds especially in the manufacturing chemistry. Therefore, both of the tautomeric forms of the compounds having such groups in their molecule are included in the scope of this invention and designated inclusively with one expression "thiazolyl" and represented by the formula:

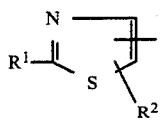

(wherein R¹ and R² are each as defined above) only for the convenient sake throughout this specification.

In the above and subsequent descriptions of this specification, suitable examples and illustration of the various definitions which this invention intends to include within the scope thereof are explained in details as follows.

The term "lower" is used to intend a group having 1 to 6 carbon atoms, unless otherwise provided.

"Protective group" in the "protected amino" may include a conventional N-protective group such as acyl, substituted or unsubstituted ar(lower)alkyl (e.g. benzyl, benzhydryl, trityl, 4-methoxybenzyl, 3,4-dimethoxybenzyl, etc.), halo(lower)alkyl (e.g. trichloromethyl, trichloroethyl, trifluoromethyl, etc.), tetrahydropyranyl, substituted phenylthio, substituted alkylidene, substituted aralkylidene, substituted cycloalkylidene, or the like.

Suitable acyl for the N-protective group may be aliphatic acyl group and acyl group containing an aromatic or heterocyclic ring. And, suitable examples of the said acyl may be lower alkanoyl (e.g., formyl, acetyl, propionyl, butyryl, isobutyryl, valeryl, isovaleryl, oxalyl, succinyl, pivaloyl, etc.), preferably one having 1 to 4 carbon atom(s), more preferably one having 1 to 2 carbon atom(s);

lower alkoxycarbonyl having 2 to 7 carbon atoms (e.g., methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, etc.), preferably one having 2 to 6 carbon atoms;

lower alkanesulfonyl (e.g., mesyl, ethanesulfonyl, propanesulfonyl, isopropanesulfonyl, butanesulfonyl, etc.);

arenesulfonyl (e.g., benzenesulfonyl, tosyl, etc.);

aroyl (e.g., benzoyl, toluoyl, naphthoyl, phthaloyl, indancarbonyl, etc.);

ar(lower)alkanoyl (e.g., phenylacetyl, phenylpropionyl, etc.);

ar(lower)alkoxycarbonyl (e.g., benzyloxycarbonyl, phenethyloxycarbonyl, etc.); and the like.

The acyl as stated above may have 1 to 3 suitable substituent(s) such as halogen (e.g., chlorine, bromine, iodine or fluorine), hydroxy, cyano, nitro, lower alkoxy (e.g., methoxy, ethoxy, propoxy, isopropoxy, etc.), lower alkyl (e.g., methyl, ethyl, propyl, isopropyl, butyl, etc.), lower alkenyl (e.g., vinyl, allyl, etc.), aryl (e.g., phenyl, tolyl, etc.), or the like, and preferable example is mono(or di or tri)halo(lower)alkanoyl (e.g., chloroacetyl, dichloroacetyl, trifluoroacetyl, etc.), mono(or di or tri)halo(lower)alkoxycarbonyl (e.g., trichloroethoxy carbonyl, etc.).

And further, the reaction product of a silan, boron, aluminium or phosphorus compound with the amino group may also be included in the N-protective group. Suitable examples of such compounds may be trimethylsilyl chloride, trimethoxysilyl chloride, boron trichloride, butoxyboron dichloride, aluminum trichloride, diethoxy aluminum chloride, phosphorus dibromide, phenylphosphorus dibromide, or the like.

"Halogen" may be chlorine, bromine, iodine or fluorine, and preferred one is chlorine or bromine.

"Lower alkyl" includes a residue of straight or branched alkane having 1 to 6 carbon atoms such as methyl, ethyl, propyl, isopropyl, butyl, isobutyl, t-butyl, pentyl, neopentyl, hexyl and the like, and preferably the one having 1 to 4 carbon atoms.

"Lower alkoxy" includes straight or branched one having 1 to 6 carbon atoms such as methoxy, ethoxy, propoxy, isopropoxy, butoxy, isobutoxy, tert-butoxy, pentyloxy, hexyloxy and the like, and preferably the one having 1 to 4 carbon atoms.

"Lower alkylthio" includes straight or branched one having 1 to 6 carbon atoms such as methylthio, ethylthio, propylthio, isopropylthio, butylthio, isobutylthio, tert-butylthio, pentylthio, hexylthio and the like, and preperably the one having 1 to 4 carbon atoms.

"Acyl" moiety in the "acyloxymethyl" may be lower alkanoyl (e.g. formyl, acetyl, propionyl, butyryl, isobutyryl, isovaleryl, pivaroyl, etc.), aroyl (e.g. benzoyl, toluoyl, xyloyl, naphthoyl, etc.), carbamoyl, N-protected carbamoyl or the like. The protective group of the above N-protected carbamoyl may be referred to those as exemplified in the explanation of the protected amino, and the preferable example is mono(or di or tri)halo(lower)alkanoyl (e.g. chloroacetyl, dichloroacetyl, trifluoroacetyl, etc.).

"Heterocyclic" moiety in the "heterocyclicthiomethyl" group may include unsaturated 5 to 6-membered heterocyclic group containing at least one hetero atom selected from oxygen, sulfur and nitrogen atoms.

And, preferable heterocyclic group may be the one such as unsaturated 5 to 6-membered heterocyclic group containing 1 to 2 oxygen atom(s), for example, furyl;

unsaturated 5 to 6-membered heterocyclic group containing 1 to 4 nitrogen atom(s), for example, pyrrolyl, imidazoyl, pyrazolyl, pyridyl, picolyl, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

unsaturated 5 to 6-membered heterocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

unsaturated 5 to 6-membered heterocyclic group containing 1 to 2 sulfur atom(s) and 1 to 3 nitrogen atom(s), for example, thiazolyl, isothiazolyl, thiadiazolyl (e.g., 1,2,4-thiadiazolyl, 1,3,4-thiadiazolyl, 1,2,5-thiadiazolyl, etc.), etc.; and the like.

These heterocyclic group may be substituted with lower alkyl as exemplified before or lower alkenyl such as vinyl, allyl, 1-propenyl, isopropenyl, butenyl, isobutenyl, pentenyl, hexenyl and the like.

"Functionally modified carboxy" may include esterified carboxy, amidated carboxy or the like.

Suitable examples of "the ester" and "ester moiety" in the "esterified carboxy" may be lower alkyl ester (e.g., methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.);

lower alkenyl ester (e.g., vinyl ester, allyl ester, etc.);

lower alkynyl ester (e.g., ethynyl ester, propynyl ester, etc.);

lower alkoxy(lower)alkyl ester (e.g., methoxymethyl ester, ethoxymethyl ester, isopropoxymethyl ester, 1-methoxyethyl ester, 1-ethoxyethyl ester, etc.);

lower alkylthio(lower)alkyl ester (e.g., methylthiomethyl ester, ethylthiomethyl ester, ethylthioethyl ester, isopropylthiomethyl ester, etc.);

halo(lower)alkyl ester (e.g., 2-idodoethyl ester, 2,2,2-trichloroethyl ester, etc.);

lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.);

lower alkanesulfonyl(lower)alkyl ester (e.g., mesylmethyl ester, 2-mesylethyl ester, etc.);

ar(lower)alkyl, for example, phenyl(lower)alkyl ester which may have one or more suitable substituent(s) (e.g., benzyl ester, 4-methoxybenzyl ester, 4-nitorbenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.);

aryl ester which may have one or more suitable substituent(s) (e.g., phenyl ester, tolyl ester, t-butylphenyl ester, xylyl ester, mesityl ester, cumenyl ester, salicyl ester, etc.);

an ester with a silyl compound such as tri(lower)alkylsilyl compound, di(lower)alkylalkoxysilyl compound or tri(lower)alkoxysilyl compound, for example, tri(lower)alkylsilyl ester (e.g., trimethyl silyl ester, triethylsilyl ester, etc.), di(lower)alkylalkoxy silyl ester (e.g., dimethylmethoxysilyl ester, dimethylethoxysilyl ester, diethylmethoxysilyl ester, etc.) or tri(lower)alkoxysilyl ester (e.g., trimethoxysilyl ester, triethoxysilyl ester, etc.), or the like.

More particularly, the preferable example of ester may be nitrophenyl(lower)alkyl ester (e.g., 4-nitrobenzyl ester, 4-nitrophenethyl ester, lower alkyl ester (e.g., methyl ester, ethyl ester, propyl ester, isopropyl ester, butyl ester, isobutyl ester, tert-butyl ester, pentyl ester, neopentyl ester, hexyl ester, etc.), etc.).

More particularly, the preferable examples of $R^1$ to $R^6$ are illustrated as follows.

The preferable examples of $R^1$ may be amino or acylamino [more preferably, lower alkanoylamino (e.g. formamido, acetamido, propionamido, butyramido, isobutyramido, valeramido, isovaleramido, etc.)].

The preferable examples of $R^2$ may be halogen (more preferably, chlorine or bromine) or lower alkyl (e.g., methyl, ethyl, propyl, isopropyl, butyl, etc.).

The preferable example of $R^3$ may be lower alkyl (e.g., methyl, ethyl, propyl, isopropyl, butyl, etc.).

The preferable examples of $R^4$ may be hydrogen, lower alkyl (e.g., methyl, ethyl, etc.) or lower alkoxy (e.g., methoxy, ethoxy, etc.).

The preferable examples of $R^5$ may be hydrogen, hydroxymethyl, acyloxymethyl [more preferably, benzoyloxymethyl, carbamoyloxymethyl, trihalo(lower)alkanoylcarbamoyloxymethyl (e.g., trichloroacetylcarbamoyloxymethyl, etc.)], tetrazolylthiomethyl which may have a lower alkyl (e.g., 1H-tetrazol-5-ylthiomethyl, 1-methyl-1H-tetrazol-5-ylthiomethyl, etc.) or thiadiazolylthiomethyl which may have a lower alkyl (e.g., 1,3,4-thiadiazol-2-ylthiomethyl, 5-methyl-1,3,4-thiadiazol-2-ylthiomethyl, etc.).

The preferable example of $R^6$ may be esterified carboxy [more preferably, nitrophenyl(lower)alkoxycarbonyl (e.g., p-nitrobenzyloxycarbonyl, etc.)].

With regard to the terms "protected amino" for $R^1$ and "functionally modified carboxy" for $R^6$, it is to be understood that these groups bear the meaning not only in synthetic manufacture of the object compound by chemical process(es), but also in physiological and pharmaceutical properties of the object compound per se. That is, in the meaning of the synthetic manufacture, free amino group for $R^1$ and/or free carboxy group for $R^6$ may be transformed into the "protected amino" and/or "functionally modified carboxy" as mentioned above before conducting the reactions for preventing any possible undesired side reaction(s), and the "protected amino" and/or "functionally modified carboxy" group in the resultant compound may be regenerated into the corresponding free amino and/or carboxy group after the reaction is conducted. This will be apparent from the explanation of the processes in the following.

On the other hand, in the meaning of the physiological and pharmaceutical properties of the object compound, the compound bearing the "protected amino" and/or "functionally modified carboxy" group is optionally used for improving the properties such as solubility, stability, absorbability, toxicity of the particularly active object compound bearing the free amino and/or carboxy group. In this case, the "protected amino" and/or "functionally modified carboxy" group is not transformed artificially into the corresponding amino and/or carboxy group before the compound is administered to human being and animals.

Suitable "pharmaceutically acceptable salt" includes conventional non-toxic salt, and may be a salt with an inorganic base or acid, for example, a metal salt such as an alkali metal salt (e.g. sodium salt, potassium salt, etc.) and an alkaline earth metal salt (e.g. calcium salt, magnesium salt, etc.), ammonium salt, an inorganic acid salt (e.g. hydrochloride, hydrobromide, sulfate, phosphate, carbonate, bicarbonate, etc.), a salt with an organic base or acid, for example, an amine salt (e.g. trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tris(hydroxymethylamino)methane salt, phenethylbenzylamine salt, etc.), an organic carboxylic or sulfonic acid salt (e.g. acetate, maleate, lactate, tartrate, mesylate, benzenesulfonate, tosylate, etc.), a basic or acidic amino acid salt (e.g. arginine salt, aspartic acid salt, glutamic acid salt, lysine salt, serine salt, etc.) and the like.

It is well known in the pharmaceutical field that the active drug, when it has any undesired physiological or pharmaceutical property such as solubility, stability, absorbability, etc., is converted into modified derivative thereof for improving such undesired properties, and then said derivative, upon administration to a patient, exhibits the active efficacy by being converted in the body to the parent drug. In this meaning, the term "pharmaceutically acceptable bioprecursor" used throughout this specification is intended to fundamentally mean all of the modified derivatives, which have structural formulae different from those of the active compounds of this invention, but are converted in the body to the active compound of this invention upon administration, and also to mean the derivatives which are sometimes derived physiologically from the compounds of this invention in the body and exhibit antimicrobial efficacy.

The compound (I) of this invention can be prepared by processes as shown in the following scheme.

PROCESS A

N-Acylation

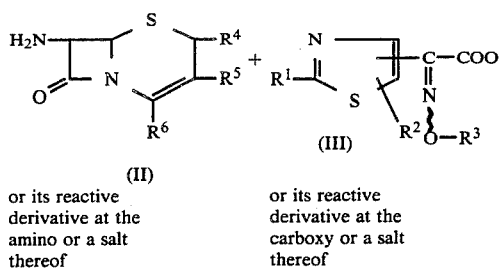

(II)
or its reactive derivative at the amino or a salt thereof (III)
or its reactive derivative at the carboxy or a salt thereof

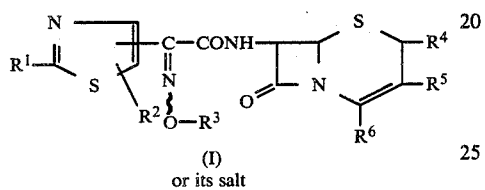

(I)
or its salt

PROCESS B

Elimination of Amino-Protective Group

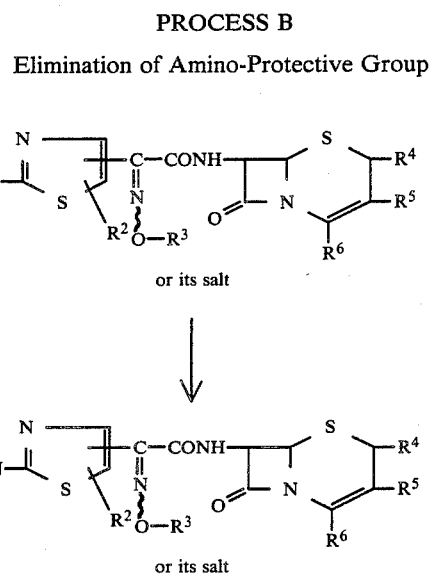

(Ib')
or its salt (Ib)
or its salt

PROCESS C

O-Acylation

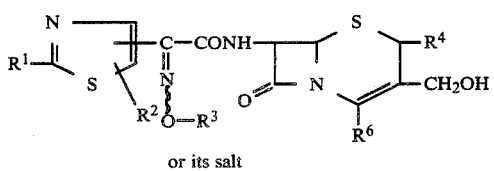

(Ic')
or its salt

R⁷—OH
or its reactive derivative
or its salt

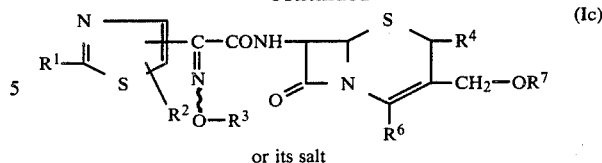

(Ic)
or its salt

PROCESS D

Elimination of Carbamoyl-Protective Group

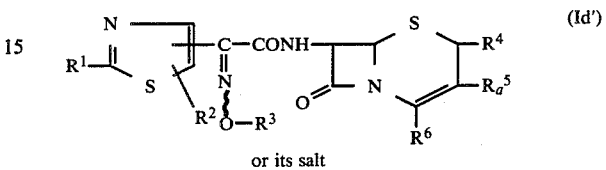

(Id')
or its salt

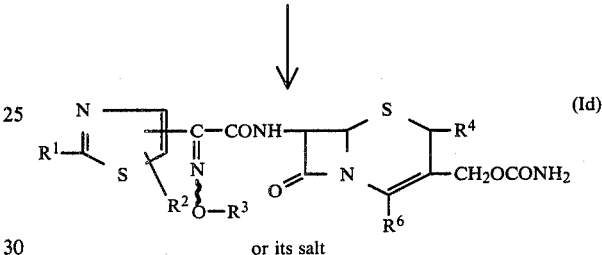

(Id)
or its salt

PROCESS E

Carboxy Formation

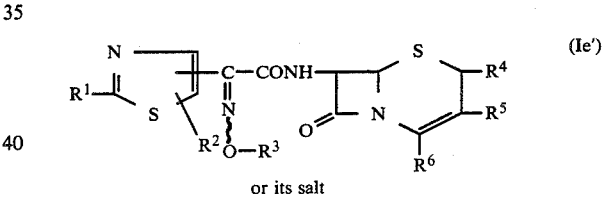

(Ie')
or its salt

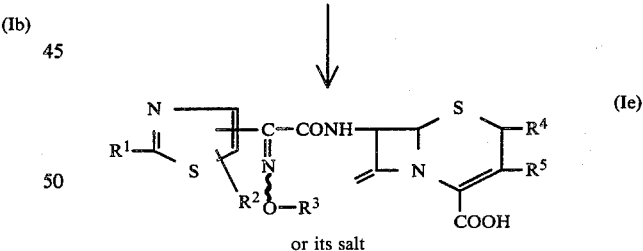

(Ie)
or its salt wherein
$R^1$, $R^2$, $R^3$, $R^4$, $R^5$ and $R^6$ are each as defined above,
$R_a^1$ is protected amino,
$R_a^5$ is N-protected carbamoyloxymethyl,
$R_a^6$ is functionally modified carboxy, and
$R^7$ is acyl The above processes will be explained in detail in the following.

PROCESS A

N-Acylation

A compound (I) or its salt can be prepared by reacting a compound (II) or its reactive derivative at the amino or a salt thereof with a compound (III) or its reactive derivative at the carboxy or a salt thereof according to a conventional manner of so-called amidation reaction well known in β-lactam chemistry.

The starting compound (III) includes new one, and the new compound (III) can be prepared according to the methods as explained hereinafter in this specification.

Suitable reactive derivative at the amino group of the compound (II) may include a conventional reactive derivative as used in a wide variety of amidation reaction, for example, isocyanato, isothiocyanato, a derivative formed by the reaction of a compound (II) with a silyl compound (e.g., trimethylsilylacetamide, bis(trimethylsilyl)acetamide, etc.), with an aldehyde compound (e.g. acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthaldehyde, furfural, thiophenecarboaldehyde, etc., or the corresponding hydrate, acetal hemiacetal or enolate thereof), with a ketone compound (e.g. acetone, methyl ethyl ketone, methyl isobutyl ketone, acetylacetone, ethyl acetoacetate, etc., or the corresponding ketal, hemiketal or enolate thereof), with phosphorus compound (e.g. phosphorus oxychloride, phosphorus chloride, etc.), or with a sulfur compound (e.g. thionyl chloride, etc.), and the like.

Suitable salt of the compound (II) may be referred to those as exemplified for the compound (I).

Suitable reactive derivative at the carboxy group of the compound (III) includes conventional ones, for example, an acid halide, an acid anhydride, an activated amide, an activated ester, and the like, and preferable acid halide such as acid chloride, acid bromide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.); a symmetrical acid anhydride; an activated acid amide with imidazole, 4-substituted imidazole, dimethylpyrazole, triazole or tetrazole; an activated ester (e.g. cyanomethyl ester, methoxymethyl ester, dimethylaminomethyl ester, vinyl ester propargyl ester, p-nitrophenyl ester, 2,4-dinitrophenyl ester, trichlorophenyl ester, pentachlorophenyl ester, mesylphenyl ester, phenylazophenyl ester, phenyl thioester p-nitrophenyl thioester, p-cresyl thioester, carboxymethyl thioester, pyranyl ester, pyridyl ester, piperidyl ester, 8-quinolyl thioester, an ester with a N-hydroxy compound such as N,N-dimethylhydroxylamine, 1-hydroxy-2-(1H)-pyridone, N-hydroxy-succinimide, N-hydroxyphthalimide, 1-hydroxybenzotriazole, 1-hydroxy-6-chlorobenzotriazole, etc.), and the like.

Suitable salt of the compound (III) may include a salt with an inorganic base such as alkali metal salt (e.g. sodium salt, potassium salt, etc.) and an alkaline earth metal salt (e.g. calcium salt, magnesium salt, etc.), a salt with an organic base such as tertiary amine (e.g. trimethylamine salt, triethylamine salt, N,N-dimethylaniline salt, pyridine salt, etc.), a salt with an inorganic acid (e.g. hydrochloride, hydrobromide, etc.) and the like.

The suitable reactive derivatives of the compounds (II) and (III) can be optionally selected from the above according to the kind of the compounds (II) and (III) to be used practically, and to the reaction conditions.

The reaction is usually carried out in a conventional solvent such as water, acetone, dioxane, acetonitrile, chloroform, benzene, methylene chloride, ethylene chloride, tetrahydrofuran, ethyl acetate, N,N-dimethylformamide, pyridine or any other solvent which does not adversely influence the reaction, or an optional mixture thereof. The reaction temperature is not critical and the reaction is preferably carried out under cooling to under heating.

When the acylating agent (III) is used in a form of free acid or salt in this reaction, the reaction is preferably carried out in the presence of a condensing agent such as a carbodiimide compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), a bisimidazolide compound (e.g. N,N'-carbonylbis(2-methylimidazole), etc.), an imine compound (e.g. pentamethyleneketene-N-cyclohexylimine, diphenylketene-N-cyclohexylimine, etc.), an olefinic or acetylenic ether compound (e.g. ethoxyacetylene, β-chlorovinylethyl ether, etc.), 1-(4-chlorobenzenesulfonyloxy)-6-chloro-1H-benzotriazole, N-ethylbenzisoxazolium salt, N-ethyl-5-phenylisoxazolium-3'-sulfonate, a phosphorus compound (e.g. polyphosphoric acid trialkyl phosphite, ethyl polyphosphate, isopropyl polyphosphate, phosphorus oxychloride, phosphorus trichloride, diethylchlorophosphite, orthophenylene chlorophosphite, etc.), thionyl chloride, oxalyl chloride, Vilsmeier reagent prepared by the reaction of N,N-dimethylformamide with thionyl chloride, phosphorus oxychloride, phosgene or the like.

With regard to the geometry of the compound (I) produced by this process, it is to be noted that there seems to be stereoselectivity between syn and anti isomers.

In order to obtain a syn isomer of the compound (I) selectively and in high yield, it is preferable to use a syn-isomer of the carboxylic acid (III), and to conduct the reaction under a selected reaction condition. That is, a syn isomer of the compound (I) can be obtained selectively and in high yield by conducting the reaction of a compound (II) with a syn isomer of the carboxylic acid (III), for example, in the presence of a Vilsmeier reagent as mentioned above and under around neutral condition.

The object compound (I) and salt thereof are useful as an antimicrobial agent, and a part thereof can also be used as a starting meterial in the following processes.

PROCESS B

Elimination of Amino-Protective Group

A compound (Ib) or its salt can be prepared by subjecting a compound (Ib') or its salt to elimination reaction of the protective group in the protected amino group for $R_a^1$.

The elimination reaction may be conducted in accordance with a conventional method such as hydrolysis, reduction or the like. These methods may be selected according to the kind of the protective group to be eliminated.

The hydrolysis may include a method using an acid (acidic hydrolysis), a base (basis hydrolysis) or hydrazine, and the like.

Among these methods, hydrolysis using an acid is one of the common and preferable methods for eliminating the protective group such as an acyl group, for example, substituted or unsubstituted lower alkanoyl, substituted or unsubstituted lower alkoxycarbonyl, substituted or unsubstituted ar(lower) alkoxycarbonyl, lower cycloalkoxycarbonyl, substituted phenylthio, substituted alkylidene, substituted aralkylidene, substituted cycloalkylidene or the like. Suitable acid to be used in this acidic hydrolysis may include an organic or inorganic acid such as formic acid, trifluoroacetic acid, benzenesulfonic acid, p-toluenesulfonic acid, hydrochloric acid, cation-exchange resin, and the like. Preferable acid is the one which can easily be separated out from the reaction product by a conventional manner such as neturalization or distillation under reduced pressure, for example, formic acid, trifluoroacetic acid, hydrochloric acid or the like. The acid suitable for the reaction can be selected in consideration of the chemical property of the starting compound (Ib') and the product (Ib) as well as the kind of the protective group to be eliminated. The acidic hydrolysis can be conducted in the presence or absence of a solvent. Suitable solvent may be a conventional organic solvent, water or a mixture thereof, which does not adversely influence this reaction. The acidic hydrolysis using trifluoroacetic acid is usually accelerated by addition of anisole.

The hydrolysis using a base can be applied for eliminating the protective group such as an acyl group, preferably, for example, haloalkanoyl (e.g. trifluoroacetyl, etc.) and the like. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as alkali metal acetate (e.g. sodium acetate, potassium acetate, etc.), trialkylamine (e.g. trimethylamine, triethylamine, etc.), picoline, N-methylpyrrolidine, N-methylmorpholine, 1,5-diazabicyclo[4,3,0]-5-nonene, 1,4-diazabicyclo[2,2,2]-octane, 1,5-diazabicyclo[5,4,0]-7-undecene, anion-exchange resin or the like. The hydrolysis using a base is often carried out in water or a conventional organic solvent or a mixture thereof.

The hydrolysis using hydrazine can be applied for eliminating the protective group such as dibasic acyl, for example, succinyl, phthaloyl or the like.

The reduction can be applied for eliminating the protective group such as acyl, for example, halo(lower)alkoxycarbonyl (e.g. trichloroethoxycarbonyl, etc.), substituted or unsubstituted ar(lower)alkoxycarbonyl (e.g. benzyloxycarbonyl, p-nitrobenzyloxycarbonyl, etc.), 2-pyridylmethoxycarbonyl, etc., aralkyl (e.g. benzyl, benzhydryl, trityl, etc.) and the like. Suitable reduction may include, for example, reduction using an alkali metal borohydride (e.g. sodium borohydride, etc.), conventional catalytic hydrogenolysis and the like.

And further, the protective group such as halo(lower)alkoxycarbonyl or 8-quinolyloxycarbonyl can be eliminated by treatment with a heavy metal such as copper, zinc or the like.

The reaction temperature is not critical and may optionally be selected in consideration of the chemical property of the starting compound and reaction product as well as the kind of the N-protective group and the method to be applied, and the reaction is preferably carried out under a mild condition such as under cooling, at ambient temperature or slightly elevated temperature.

In case that this reaction is applied to a compound (Ib') where $R^5$ is N-protected carbamoyloxymethyl group, the carbamoyl-protective group may occasionally be eliminated by this reaction according to the kind of the carbamoyl-protective group and the reaction conditions, and such a case is also included in the scope of this invention.

And further this process includes in its scope the cases that the functionally modified carboxy for $R^6$ is simultaneously transformed into the free carboxy group in the course of the above reaction of in the posttreatment.

As to this process, it is to be understood that the purpose of this process lies in providing the generally more active compound (I) wherein $R^1$ is amino group by eliminating the protective group of the compound (Ib') prepared by the other processes as mentioned above or below.

PROCESS C

O-Acylation

A compound (Ic) or its salt can be prepared by reacting a compound (Ic') or its salt with a compound (IV) or its reactive derivative or its salt.

The acyl moiety for $R^7$ is to be referred to those as exemplified above for the acyl moiety in the acyloxymethyl group for $R^5$ of the compound (I).

The reactive derivative of the compound (IV) may be an acyl halide, anhydride, azide, activated ester, activated amide, isocyanic acid, isocyanate, and the like, particulars of which are to be referred to those as exemplified before for the compound (III) in the Process A preferably an acyl halide such as lower alkanoyl halide (e.g. acetyl chloride, etc.), aroyl halide (e.g. benzoyl chloride, etc.), and mono(or di or tri)halo(lower)alkanoyl isocyanate (e.g. chloroacetylisocyanate, dichloroacetylisocyanate, trichloroacetylisocyanate, etc.).

The reaction is usually carried out in a conventional solvent such as dimethylformamide, chloroform, methylene chloride or any other solvent which does not adversely influence the reaction. The reaction temperature is not critical and the reaction may be preferably carried out under cooling or at an ambient or somewhat elevated temperature.

In case that the acyl halide is used as an acylating agent, the reaction is generally conducted in the presence of a base as exemplified in the above Process B.

PROCESS D

Elimination of Carbamoyl-Protective Group

A compound (Id) or its salt can be prepared by subjecting a compound (Id') or its salt to elimination reaction of the protective group in the protected carbamoyloxymethyl group for $R_a^5$.

This elimination reaction may be conducted in the same manner as the above Process B, i.e. the elimination reaction of the amino-protective group for $R_a^1$, and particulars of which are to be referred to the aforementioned Process B.

In case that this reaction is applied to a compound (Id') where $R^1$ is a protected amino group, the amino-protective group may occasionally be eliminated by this reaction in accordance with the kind of the said amino-protective group and the reaction conditions, and such a case is also included in the scope of this invention.

And further, this process includes in its scope the case that the functionally modified carboxy group for $R^6$ is transformed into free carboxy group in the course of the reaction or post-treatment.

As to this process, it is to be understood that the purpose of this process lies in providing the generally more active compound (I) where $R^5$ is carbamoyloxymethyl group by eliminating the protective group in the protected carbamoyloxymethyl group of the compound (Id')

PROCESS E

Carboxy Formation

The compound (Ie) or its salt can be prepared by transforming the functionally modified carboxy of the compound (Ie') or its salt, into a free carboxy.

This process is to provide a free carboxy compound (Ie) or its salt, which generally exhibits higher antimicrobial activities as compared with the corresponding functionally modified carboxy compound (Ie') or its salt.

The preferred functionally modified carboxy for $R_a^6$ in the compound (Ie') may be an esterified carboxy group as exemplified for $R^6$ of the compound (I).

The method to be applied to this process includes conventional ones each as hydrolysis, reduction and the like.

The method of hydrolysis includes a conventional one using an acid, base, and the like.

Suitable examples of the acid and base are to be referred to those as exemplified in the above Process B, and the acidic or basic hydrolysis can be carried out in a similar manner to that of the Process B.

The method of the reduction for this process may be carried out in a similar manner to that of the above Process B.

This process includes within its scope of the cases that the protective group in the protected amino for $R^1$ and/or the protective group in the protected carbamoyloxymethyl for $R^5$ is eliminated in the course of the reaction or the post-treatment.

The compound obtained in accordance with the processes as explained above can be isolated and purified in a conventional manner.

In case that the object compound (I) has free amino group for $R^1$ and/or free carboxy group for $R^6$, it may be transformed into its pharmaceutically acceptable salt by a conventional method.

The object compound (I), its pharmaceutically acceptable salt and bioprecursor thereof exhibit high antimicrobial activities inhibiting the growth of a wide variety of pathogenic microorganisms including Gram-positive and Gram-negative bacteria and are useful as antimicrobial agent.

In order to show the utility of the object compound (I), the test data of some representative compounds (I) are shown in the following.

1. IN VITRO ANTIBACTERIAL ACTIVITY (1) Test method:

In vitro antibacterial activity was determined by the two-fold agar-plate dilution method as described below.

One loopful of an overnight culture of each test strain in Trypticase-soy broth was streaked on heart infusion agar (HI-agar) containing graded concentrations of the test compound and incubated at 37° C. for 20 hours. The minimal inhibitory concentration (MIC) was expressed in $\mu g/ml$.

(2) Test compounds:

No. 1. 7-[2-(2-(2-amino-5-bromothiazol-4-yl)-2-methoxyiminoacetamido]-3-(1,3,4-thiadiazol-2-ylthiomethyl)-3-cephem-4-carboxylic acid (syn isomer)

2.       7-[2-(2-amino-5-bromothiazol-4-yl)-2-methoxyiminoacetamide]-3-(5-methyl-1,3,4-thiadiazol-2-ylthiomethyl)-3-cephem-4-carboxylic acid (syn isomer)

3.       7-[2-(2-amino-5-bromothiazol-4-yl)-2-methoxyiminoacetamido]-3-(1-methyl-1H-tetrazol-5-ylthiomethyl)-3-cephem-4-carboxylic acid (syn isomer)

4.       7-[2-(2-amino-5-bromothiazol-4-yl)-2-methoxyiminoacetamido]-3-benzoyloxymethyl-3-cephem-4-carboxylic acid (syn isomer)

5.       7-[2-(2-amino-5-chorothiazol-4-yl)-2-methoxyiminoacetamido]-3-(1,3,4-thiadiazol-2-ylthiomethyl)-3-cephem-4-carboxylic acid (syn isomer)

| | (3) Test results: MIC ($\mu g/ml$) | | | | |
|---|---|---|---|---|---|
| | Compound No. | | | | |
| Test Strains | 1 | 2 | 3 | 4 | 5 |
| Staphylococcus aureus 209P JC-1 | 1.56 | 3.13 | 3.13 | 1.56 | 3.13 |
| Escherichia coli NIHJ JC-2 | 0.78 | 1.56 | 1.56 | 6.25 | 1.56 |
| Proteus vulgaris IAM-1025 | 6.25 | 12.5 | 12.5 | 12.5 | 1.56 |
| Klebsiella pneumoniae 20 | 0.78 | 3.13 | 0.39 | 1.56 | 0.39 |
| Proteus mirabilis 18 | 0.78 | 6.25 | 3.13 | 3.13 | 0.78 |
| Pseudomonus aeruginosa NCTC-10490 | 3.13 | 6.25 | 3.13 | 6.25 | 1.56 |

For prophylactic and/or therapeutic administration, the compound (I) of the present invention is used in the form of conventional pharmaceutical preparation which contains said compound, as an active ingredient, in admixture with pharmaceutically acceptable carriers such as an organic or inorganic solid or liquid excipient which is suitable for oral, parenteral or external administration. The pharmaceutical preparations may be in solid form such as capsule, tablet, dragee, ointment or suppository, or in liquid form such as solution, suspension, or emulsion. If needed, there may be included in the above preparations auxiliary substances, stabilizing agents, wetting or emulsifying agents, buffers and the other commonly used additives.

While the dosage of the compounds may vary from and also depend upon the age and conditions of the patient, a kind of disease and a degree of the infection, and further a kind of the compound (I) to be applied, etc., an average single dose of about 50 mg., 100 mg., 250 mg. and 500 mg. of the compound (I) is sufficient for treating infectious diseases caused by pathogenic bacteria. In general, the compound (I) can be administered in an amount between 1 mg/kg and 100 mg/kg, preferably 5 mg/kg and 50 mg/kg.

The starting compound (III) or its ester or a salt thereof are novel and can be prepared by the methods illustrated below.

PROCESS 1

Halogenation

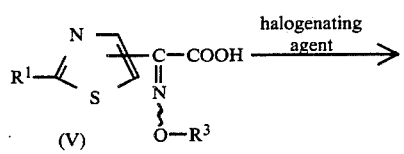

(V)

or its ester of salt

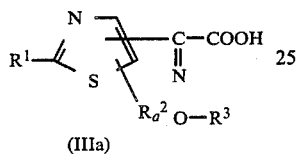

(IIIa)

or its ester or salt

PROCESS 2

Etherification

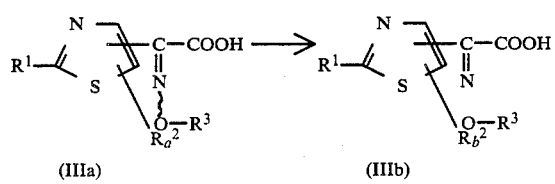

(IIIa)          (IIIb)

or its ester of salt      or its ester or salt

PROCESS 3

Elimination of Amino-Protective group

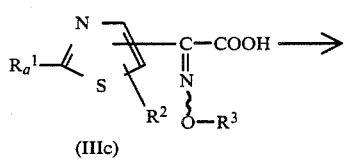

(IIIc)

or its ester or salt

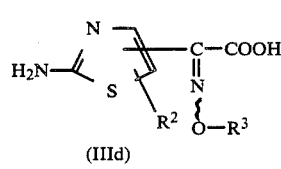

(IIId)

or its ester or salt

PROCESS 4

Carboxy Formation

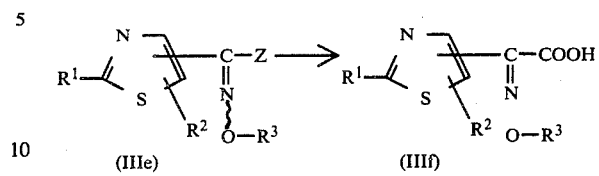

(IIIe)          (IIIf)

or its salt        or its salt

PROCESS 5

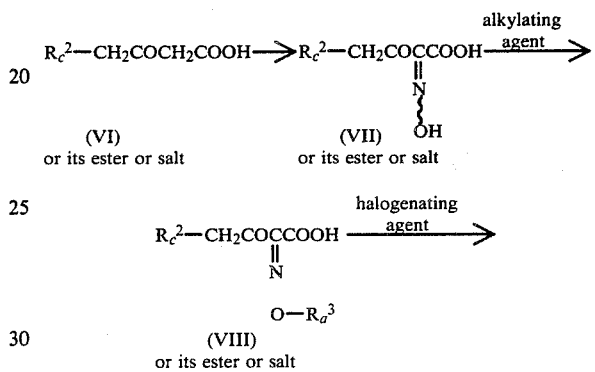

(VI)          (VII)

or its ester or salt    or its ester or salt

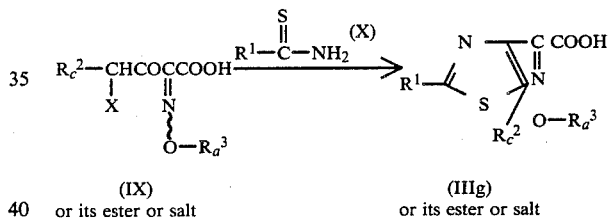

(VIII)

or its ester or salt

(IX)          (IIIg)

or its ester or salt    or its ester or salt wherein
$R^1$, $R^2$ and $R^3$ are each as defined above,
$R_a^1$ is protected amino,
$R_a^2$ is halogen,
$R_b^2$ is lower alkoxy or lower alkylthio,
$R_c^2$ is lower alkyl,
$R_a^3$ is lower alkyl,
X is halogen, and
Z is esterified carboxy.

Each of the above processes are explained in the following.

PROCESS 1

Halogenation

The compound (III$_a$) or its ester or salt can be prepared by reacting a compound (V) or its ester or salt with a conventional halogenating agent such as chlorine, bromine, N-chlorosuccinimide, N-bromosuccinimide, trichloroisocyanuric acid and the like. The reaction is usually conducted in a solvent such as chloroform, methylenechloride, dichloroethane or any other solvent which does not adversely influence the reaction. The reaction temperature is not critical and the reaction is preferably carried out under cooling to under heating.

PROCESS 2

Etherification

The compound (III$_b$) or its ester or salt can be prepared by reacting a compound (III$_a$) or its ester or salt with alkali metal lower alkoxide (e.g. sodium methoxide, potassium methoxide, etc.), alkali metal lower alkanethiolate (e.g. sodium methanethiolate, etc.), or lower alkanol or lower alkanethiol in the presence of a base such as alkali metal hydroxide (e.g. sodium hydroxide, potassium hydroxide, etc.), alkali metal lower alkoxide (e.g. sodium methoxide, potassium methoxide, etc.) and the like. The reaction is usually conducted in a solvent such as benzene, xylene or any other solvent which does not adversely influence the reaction. The reaction temperature is not critical and the reaction is preferably carried out under cooling to under heating. In case that the lower alkanol or lower alkanethiol is liquid, it can be preferably used as a solvent, too.

PROCESS 3

Elimination of Amino-Protective Group

The compound (III$_d$) or its ester or salt can be prepared by subjecting a compound (III$_c$) or its ester or salt to the elimination reaction of the amino-protective group. This reaction may be conducted substantially in the same manner as the aforementioned Process B.

PROCESS 4

Carboxy Formation

The compound (III$_f$) or its salt can be prepared by transforming an esterified carboxy group of the compound (III$_e$) or its salt into a free carboxy group.

This reaction may be conducted substantially in the same manner as the aforementioned Process E.

PROCESS 5

In the 1st step of this process, the compound (VII) or its ester or salt can be prepared by reacting a compound (VI) or its ester or salt with a nitrosating agent. The suitable nitrosating agent may include nitrous acid and its conventional derivative such as nitrosyl halide (e.g. nitrosyl chloride, nitrosyl bromide, etc.), alkali metal nitrite (e.g. sodium nitrite, potassium nitrite, etc.), alkyl nitrite (e.g. butyl nitrite, pentyl nitrite, etc.) and the like. In case that a salt of nitrous acid is used as a nitrosating agent, the reaction is preferably carried out in the presence of an acid such as an inorganic or organic acid (e.g. hydrochloric acid, sulfuric acid, formic acid, acetic acid, etc.). The reaction is usually conducted in a solvent such as water, acetic acid, benzene, methanol, ethanol, tetrahydrofuran or any other solvent which does not adversely influence the reaction and the reaction is preferably conducted within the range of cooling to an ambient temperature.

In the 2nd step, the compound (VIII) or its ester or salt can be prepared by reacting a compound (VII) or its ester or salt with a lower alkylating agent. The suitable lower alkylating agent may include mono or di(lower-)alkyl sulfate (e.g. methyl sulfate, dimethylsulfate, diethylsulfate, etc.), diazomethane and the like.

The reaction is usually carried out in a solvent such as water, acetone, ethanol, diethyl ether, dimethylformamide or any other solvent which does not adversely influence the reaction, within a temperature range of cooling to heating.

In the 3rd step, the compound (IX) or its ester or salt can be prepared by reacting the compound (VIII) or its ester or salt with a halogenating agent.

The suitable halogenating agent may be halogen (e.g. bromine, chlorine, etc.), sulfuryl halide (e.g. sulfuryl bromide, sulfuryl chloride, etc.), N-halosuccinimide (e.g. N-bromosuccinimide, N-chlorosuccinimide, etc.) or the like.

The reaction is usually carried out in a solvent such as acetone, diethyl ether, N,N-dimethylformamide, tetrahydrofuran, ethyl acetate, acetic acid or any other solvent which does not adversely influence the reaction. The reaction temperature is not critical and the reaction may be preferably conducted within a temperature range of cooling to somewhat elevated temperature.

In the 4th step, the compound (III$_g$) or its ester or salt can be prepared by reacting a compound (IX) or its ester or salt with a thiourea compound (X).

The reaction is usually conducted in a solvent such as water, alcohol (e.g. methanol, ethanol, etc.), benzene, acetone, N,N-dimethylformamide, tetrahydrofuran, diethyl ether, dioxane or any other solvent which does not adversely influence the reaction.

The reaction temperature is not critical and the reaction may be preferably carried out within a temperature range of ambient temperature to heating.

Following Preparations and Examples are given for explaining this invention in more detail.

PREPARATION 1

(1) A solution of diethyl malonate (80 g.) in ethanol (40 ml.) was added dropwise over 20 minutes to a mixture of magnesium (12.5 g.), carbontetrachloride (0.5 ml.) and ethanol (12.5 ml.) was stirred at room temperature for 10 minutes. Diethyl ether was added dropwise to the solution and refluxed under heating for 30 minutes. To the solution was added dropwise a solution of propionyl chloride (49 g.) in diethyl ether (50 ml.) under cooling over 10 minutes, and the mixture was refluxed under heating for 30 minutes. 20% sulfuric acid (200 ml.) was added to the solution, and the diethyl ether layer was separated, washed with 10% sulfuric acid and water successively, dried over magnesium sulfate and then filtered. The filtrate was evaporated in vacuo. To the oily residue was added $\beta$-naphthalene sulfonic acid hydrate (8 g.) and the mixture was heated at 200° C. for 1 hr. After cooling, diethyl ether (100 ml.) was added to the mixture and washed with 10% aqueous sodium carbonate (100 ml.) three times. The aqueous layer was extracted with diethyl ether (100 ml.) five times, and the extract was washed with water, dried over magnesium sulfate and then distilled under reduced pressure (24 mmHg). The distillate at 100° to 110° C. was collected and distilled again under reduced pressure (25 mmHg). The distillate at 97° to 99° C. was collected to give ethyl propionylacetate (19.8 g.).

I.R. (liquid film): $\nu$max: 2980, 2940, 1730, 1620, 1460, 1420 cm$^{-1}$.

N.M.R. (CCl$_4$): $\delta$ppm: 1.03 (3H, t, J=7 Hz), 1.27 (3H, t, J=7 Hz), 2.50 (2H, q, J=7 Hz), 3.20 (2H, s), 4.15 (2H, q, J=7 Hz).

(2) Ethyl propionylacetate (14.4 g.) was added to acetic acid (19 ml.) and stirred at 5° to 10° C. To the solution was added dropwise over 40 minutes about ⅔ volume of an aqueous solution (30 ml.) of sodium nitrite (15 g.), and further water (50 ml.) was added to the solution and stirred at 25° C. for 1.5 hrs. The remaining aqueous solution of sodium nitrite was added dropwise over 10 minutes to the solution and stirred at room temperature for 2 hrs. The reaction mixture was extracted with diethyl ether (50 ml.) twice, and the extract was washed with saturated aqueous sodium bicarbonate (30 ml.) three times and saturated aqueous sodium chloride, dried over magnesium sulfate and filtered. The filtrate was evaporated in vacuo to give ethyl 2-propionyl-2-hydroxyiminoacetate (12 g.).

I.R. (liquid film): νmax: 3330, 2980, 2940, 2900, 1720, 1625, 1460 cm$^{-1}$.

N.M.R. (CCl$_4$): δppm: 1.10 (3H, t, J=7 Hz), 1.35 (3H, t, J=7 Hz), 2.80 (2H, q, J=7 Hz), 4.34 (2H, q, J=7 Hz).

(3) A mixture of ethyl 2-hydroxyimino-2-propionylacetate (10.7 g.), potassium carbonate (9.8 g.), dimethyl sulfate (7.79 g.) and ethyl acetate (70 ml.) was stirred at room temperature for an hour. Water (50 ml.) was added to the reaction mixture and stirred for 20 minutes. The ethyl acetate layer was separated, washed with water (50 ml.) twice and with an aqueous solution of sodium chloride, dried over magnesium sulfate and then filtered. The filtrate was evaporated in vacuo to give ethyl 2-methoxyimino-2-propionylacetate (14.7 g.).

N.M.R. (CCl$_4$): δppm: 1.12 (3H, t, J=7 Hz), 1.35 (3H, t, J=7 Hz), 2.77 (2H, q, J=7 Hz), 3.93 (3H, s), 4.30 (2H, q, J=7 Hz).

(4) A mixture of ethyl 2-methoxyimino-2-propionylacetate (14.7 g.), sulfuryl chloride (10.9 g.) and acetic acid (14.7 ml.) was stirred at room temperature for an hour and then at 40° C. for 2.5 hrs. Ice-water was added to the reaction mixture, adjusted to pH 6.5 and extracted with methylene chloride. The extract was washed with an aqueous solution of sodium chloride, dried over magnesium sulfate and then filtered. The filtrate was evaporated in vacuo to give ethyl 2-methoxyimino-2-(2-chloropropionyl)acetate (16.0 g.).

N.M.R. (CCl$_4$): δppm: 1.30 (3H, t, J=7 Hz), 1.60 (3H, d, J=7 Hz), 3.87 (3H, s), 4.23 (2H, q, J=7 Hz), 5.08 (1H, q, J=7 Hz).

(5) A mixture of ethyl 2-methoxyimino-2-(2-chloropropionyl)acetate (16.0 g.), thiourea (8.2 g.), sodium acetate (8.9 g.), water (50 ml.) and ethanol (50 ml.) was stirred at 40° C. for 3 hrs. Ethanol was distilled off in vacuo from the reaction mixture. Diisopropyl ether was added to the aqueous solution and stirred. The resultant precipitates were collected by filtration to give ethyl 2-(2-amino-5-methylthiazol-4-yl)-2-methoxyiminoacetate (syn isomer, 3.1 g.). The diisopropyl ether layer was separated from the filtrate, washed with water and an aqueous solution of sodium chloride successively, dried over magnesium sulfate and then filtered. The filtrate was evaporated in vacuo and the oily residue was treated with n-hexane. The precipitates were collected by filtration and washed with a small amount of diisopropyl ether to give the same product (0.9 g.) as above. Total yield 4.0 g.

I.R. (Nujol): νmax: 3430, 3280, 3110, 1715, 1625, 1535, 1510 cm$^{-1}$.

N.M.R. (DMSO-d$_6$): δppm: 1.24 (3H, t, J=7 Hz), 2.35 (3H, s), 3.85 (3H, s), 4.22 (2H, q, J=7 Hz), 6.91 (2H, broad s).

(6) A mixture of ethyl 2-(2-amino-5-methylthiazol-4-yl)-2-methoxyiminoacetate (syn isomer, 4.0 g.), 2N-aqueous sodium hydroxide (25 ml.), ethanol (30 ml.) and tetrahydrofuran (15 ml.) was stirred at room temperature for 75 minutes. The reaction mixture was adjusted to pH 6 with hydrochloric acid, and the organic solvent was distilled off in vacuo. The remaining aqueous solution was washed with ethyl acetate and adjusted to pH 3 with hydrochloric acid. The resultant precipitates were collected by filtration, washed with water and dried to give 2-(2-amino-5-methylthiazol-4-yl)-2-methoxyiminoacetic acid (syn isomer, 2.6 g.).

I.R. (Nujol): νmax: 3340, 1630, 1570 cm$^{-1}$.

N.M.R. (DMSO-d$_6$/D$_2$O): δppm: 2.33 (3H, s), 3.82 (3H, s).

(7) A mixture of 2-(2-amino-5-methylthiazol-4-yl)-2-methoxyiminoacetic acid (syn isomer, 2.6 g.), acetic anhydride (31 ml.) and formic acid (13 ml.) was stirred at room temperature for 2 hrs. and then evaporated in vacuo. The residue was dissolved in a mixture of water and ethyl acetate. The ethyl acetate layer was separated, washed with an aqueous solution of sodium chloride, dried over magnesium sulfate, treated with activated charcoal and then filtered. The filtrate was evaporated in vacuo. The oily residue was treated with n-hexane and diisopropyl ether, and the precipitates were collected by filtration to give 2-(2-formamido-5-methylthiazol-4-yl)-2-methoxyiminoacetic acid (syn isomer, 2.8 g.).

I.R. (Nujol): νmax: 3180, 3060, 1745, 1680, 1660, 1525 cm$^{-1}$.

N.M.R. (DMSO-d$_6$): δppm: 2.52 (3H, s), 3.90 (3H, s), 8.44 (1H, s).

PREPARATION 2

(1) Trichloroisocyanuric acid (6.7 g.) was added portionwise to a chilled solution of ethyl 2-(2-formamidothiazol-4-yl)-2-methoxyiminoacetate (syn isomer, 20.0 g.) in dry dimethylformamide (400 ml.) and stirred at room temperature for 2 hrs. The reaction mixture was poured into chilled water (2 l.), and the precipitates were collected by filtration, washed with water and dried to give ethyl 2-(2-formamido-5-chlorothiazol-4-yl)-2-methoxyiminoacetate (syn isomer, 18.9 g.).

I.R. (Nujol): δmax: 3100, 3050, 1740, 1700, 1680, 1560 cm$^{-1}$.

N.M.R. (CDCl$_3$): δppm: 1.43 (3H, t, J=8 Hz), 4.07 (3H, s), 4.47 (2H, q, J=8 Hz), 8.70 (1H, s), 11.93 (1H, s).

(2) 1N-Aqueous sodium hydroxide (195 ml.) was added dropwise to an aqueous suspension (190 ml.) of ethyl 2-(2-formamido-5-chlorothiazol-4-yl)-2-methoxyiminoacetate (18.9 g.) under ice-cooling and stirred for 4 hrs. The reaction mixture was washed with ethyl acetate, and ethyl acetate was added to the aqueous solution, adjusted to pH 1.0 with 6N-hydrochloric acid and then saturated with sodium chloride. The ethyl acetate layer was separated and the remaining aqueous layer was washed with ethyl acetate. The ethyl acetate layer obtained above and the washings were combined, washed with saturated aqueous sodium chloride, dried over magnesium sulfate and then evaporated in vacuo. The residue was pulverized with diisopropyl ether and the precipitates were collected by filtration and dried to give 2-(2-formamido-5-chlorothiazol-4-yl)-2-methoxyiminoacetic acid (syn isomer, 14.7 g.), m.p. 175° to 177° C.

I.R. (Nujol): νmax: 3200, 3050, 1750, 1710, 1660, 1550 cm$^{-1}$.

N.M.R. (DMSO-d$_6$): δppm: 3.97 (3H, s), 8.57 (1H, s), 12.90 (1H, s).

PREPARATION 3

(1) A small amount of benzoyl peroxide was added to a suspension of ethyl 2-(2-formamidothiazol-4-yl)-2-methoxyiminoacetate (syn isomer, 7.55 g.) and N-bromosuccinimide (5.75 g.) in dry benzene (150 ml.) and refluxed under heating for an hour. After cooling, the reaction mixture was washed with water three times, dried over magnesium sulfate, treated with activated charcoal and then evaporated in vacuo. The residue was pulverized with n-hexane, and the precipitates were collected by filtration, washed with n-hexane and water successively and dried to give ethyl 2-(2-formamido-5-bromothiazol-4-yl)-2-methoxyiminoacetate (syn isomer, 9.3 g.).

I.R. (Nujol): $\nu$max: 3200, 1750, 1740, 1560 cm$^{-1}$.

N.M.R. (CDCl$_3$): $\delta$ppm: 1.40 (3H, t, J=8 Hz), 4.07 (3H, s), 4.43 (2H, q, J=8 Hz), 8.67 (1H, s), 11.82 (1H, s).

(2) 1N-Aqueous sodium hydroxide (290 ml.) was added dropwise to an aqueous suspension (325 ml.) of ethyl 2-(2-formamido-5-bromothiazol-4-yl)-2-methoxyiminoacetate (syn isomer, 32.5 g.) under ice-cooling, and the mixture was treated in a similar manner to that of Preparation 2-(2) to give 2-(2-formamido-5-bromothiazol-4-yl)-2-methoxyiminoacetic acid (syn isomer, 21.9 g.), m.p. 165° to 167° C.

I.R. (Nujol): $\nu$max: 3200, 3050, 1750, 1710, 1660, 1550 cm$^{-1}$.

N.M.R. (DMSO-d$_6$): $\delta$ppm: 4.00 (3H, s), 8.60 (1H, s), 12.97 (1H, s).

EXAMPLE 1

(1) A mixture of dimethylformamide (0.3 ml.), phosphoryl chloride (0.35 ml.) and dry ethyl acetate (1.5 ml.) was stirred for 30 minutes under ice-cooling. Dry ethyl acetate (1.5 ml.) and 2-(2-formamido-5-bromothiazol-4-yl)-2-methoxyiminoacetic acid (syn isomer, 1.0 g.) were added to the solution and stirred for 50 minutes under ice-cooling. The solution was added dropwise to a chilled solution of 7-amino-3-(5-methyl-1,3,4-thiadiazol-2-ylthiomethyl)-3-cephem-4-carboxylic acid (1.1 g.) and trimethylsilylacetamide (2.5 g.) in dry ethyl acetate (30 ml.), and stirred at −20° to −10° C. for an hour. To the reaction mixture were added ethyl acetate (30 ml.) and water 20 ml., and the insoluble substance was filtered off. The ethyl acetate layer was separated from the filtrate, and the aqueous layer was washed with ethyl acetate. The washings and the ethyl acetate layer were combined together, washed with a saturated aqueous sodium chloride, dried over magnesium sulfate and then evaporated in vacuo. The residue was pulverized with diethyl ether, and the precipitates were collected by filtration, washed with diethyl ether and dried to give 7-[2-(2-formamido-5-bromothiazol-4-yl)-2-methoxyiminoacetamido]-3-(5-methyl-1,3,4-thiadiazol-2-ylthiomethyl)-3-cephem-4-carboxylic acid (syn isomer, 1.2 g.).

I.R. (Nujol): $\nu$max: 3300, 1780, 1680 (broad), 1540 (broad) cm$^{-1}$.

N.M.R. (DMSO-d$_6$): $\delta$ppm: 2.64 (3H, s), 3.48–3.72 (2H, broad s), 3.90 (3H, s), 4.18, 4.50 (2H, AB$_q$, J=12 Hz), 5.10 (1H, d, J=4 Hz), 5.78 (1H, d,d, J=4 Hz, 8 Hz), 8.48 (1H, s), 9.60 (1H, d, J=8 Hz), 12.80 (1H, s).

(2) Conc. hydrochloric acid (1.5 ml.) was added to a solution of 7-[2-(2-formamido-5-bromothiazol-4-yl)-2-methoxyiminoacetamido]-3-(5-methyl-1,3,4-thiadiazol-2-ylthiomethyl)-3-cephem-4-carboxylic acid (syn isomer), (1.2 g.) in methanol (30 ml.) and stirred at room temperature for 7 hrs. The reaction mixture was evaporated in vacuo. To the residue was added ethyl acetate and water was removed by evaporation. The residue was pulverized with ethyl acetate and the precipitates were collected by filtration, washed with ethyl acetate and diethyl ether successively and then dried to give 7-[2-(2-amino-5-bromothiazol-4-yl)-2-methoxyiminoacetamido]-3-(5-methyl-1,3,4-thiadiazol-2-ylthiomethyl)-3-cephem-4-carboxylic acid hydrochloride (syn isomer, 1.0 g.).

Thus obtained product (1.0 g.) was suspended in water (10 ml.) and the suspension was adjusted to pH 4.0 with saturated aqueous sodium bicarbonate. The resultant precipitates were collected by filtration, washed with chilled water and dried to give 7-[2-(2-amino-5-bromothiazol-4-yl)-2-methoxyiminoacetamido]-3-(5-methyl-1,3,4-thiadiazol-2-ylthiomethyl)-3-cephem-4-carboxylic acid (syn isomer, 720 mg.).

I.R. (Nujol): $\nu$max: 3300, 3200, 1780, 1670, 1650 1530 cm$^{-1}$.

N.M.R. (DMSO-d$_6$): $\delta$ppm: 2.66 (3H, s), 3.56, 3.76 (2H, AB$_q$, J=16 Hz), 3.86 (3H, s), 4.18, 4.52 (2H, AB$_q$, J=12 Hz), 5.10 (1H, d, J=4 Hz), 5.76 (1H, d, d, J=4 Hz, 8 Hz), 9.52 (1H, d, J=8 Hz).

EXAMPLE 2

(1) A solution of 7-amino-3-(1,3,4-thiadiazol-2-ylthiomethyl)-3-cephem-4-carboxylic acid (syn isomer, 1.1 g.) and trimethylsilylacetamide (3.4 g.) in dry ethyl acetate (30 ml.) and a mixture of dimethylformamide (0.3 ml.), phosphoryl chloride (0.35 ml.), 2-(2-formamido-5-bromothiazol-4-yl)-2-methoxyiminoacetic acid (syn isomer, 1.0 g.) and dry ethyl acetate (30 ml.) were treated in a similar manner to that of Example 1-(1) to give 7-[2-(2-formamido-5-bromothiazol-4-yl)-2-methoxyiminoacetamido]-3-(1,3,4-thiadiazol-2-ylthiomethyl)-3-cephem-4-carboxylic acid (syn isomer, 1.2 g.).

I.R. (Nujol): $\nu$max: 3300, 3050, 1780, 1680, 1540 cm$^{-1}$.

D.M.R. (DMSO-d$_6$): $\delta$ppm: 3.47–3.70 (2H, broad s), 3.80 (3H, s), 4.20, 4.57 (2H, AB$_q$, J=12 Hz), 5.08 (1H, d, J=4 Hz), 5.75 (1H, d,d, J=4 Hz, 8 Hz), 8.43 (1H, s), 9.45 (1H, s), 9.57 (1H, d, J=8 Hz), 12.73 (1H, s).

(2) 7-[2-(2-Formamido-5-bromothiazol-4-yl)-2-methoxyiminoacetamido]-3-(1,3,4-thiadiazol-2-ylthiomethyl)-3-cephem-4-carboxylic acid (syn isomer, 1.2 g.) was treated with conc. hydrochloric acid (2 ml.) in a similar manner to that of Example 1-(2) to give 7-[2-2-amino-5-bromothiazol-4-yl)-2-methoxyiminoacetamido]-3-(1,3,4-thiadiazol-2-ylthiomethyl)-3-cephem-4-carboxylic acid hydrochloride (syn isomer, 1.2 g.).

Thus obtained product (1.2 g.) was treated with saturated aqueous sodium bicarbonate in a similar manner to that of Example 1-(2) to give 7-[2-(2-amino-5-bromothiazol-4-yl)-2-methoxyiminoacetamido]-3-(1,3,4-thiadiazol-2-ylthiomethyl)-3-cephem-4-carboxylic acid (syn isomer, 850 mg.).

I.R. (Nujol): $\nu$max: 3400, 3200, 1780, 1680, 1620 (broad), 1540 (broad) cm$^{-1}$.

N.M.R. (DMSO-d$_6$): $\delta$ppm: 3.53–3.73 (2H, broad s), 3.82 (3H, s), 4.20, 4.57 (2H, AB$_q$, J=12 Hz), 5.07 (1H, d, J=4 Hz), 5.73 (1H, d, d, J=4 Hz, 8 Hz), 7.17–7.50 (2H, broad s), 9.50 (1H, d, J=8 Hz), 9.50 (1H, s).

EXAMPLE 3

(1) A solution of 7-amino-3-(1-methyl-1H-tetrazol-5-ylthiomethyl)-3-cephem-4-carboxylic acid (660 mg.) and trimethylsilylacetamide (1.3 g.) in dry ethyl acetate (23 ml.) and a mixture of dimethylformamide (0.2 ml.), phosphoryl chloride (0.24 ml.), dry ethyl acetate (10 ml.) and 2-(2-formamido-5-bromothiazol-4-yl)-2- methoxyiminoacetic acid (syn isomer, 740 mg.) were treated in a similar manner to that of Example 1-(1) to give 7-[2-(2-formamido-5-bromothiazol-4-yl)-2-methoxyiminoacetamido]-3-(1-methyl-1H-tetrazol-5-ylthiomethyl)-3-cephem-4-carboxylic acid (syn isomer, 520 mg.).

I.R. (Nujol): νmax: 3300, 3100, 1780, 1680, 1620, 1550 cm$^{-1}$.

N.M.R. (DMSO-d$_6$): δppm: 3.53–3.80 (2H, broad s), 3.97 (6H, s), 4.17–4.43 (2H, broad s), 5.10 (1H, d, J=4 Hz), 5.77 (1H, d, d, J=4 Hz, 8 Hz), 8.57 (1H, s), 9.63 (1H, d, J=8 Hz).

(2) 7-[2-(2-Formamido-5-bromothiazol-4-yl)-2-methoxyiminoacetamido]-3-(1-methyl-1H-tetrazol-5-ylthiomethyl)-3-cephem-4-carboxylic acid (syn isomer, 700 mg.) was treated with conc. hydrochloric acid (1 ml.) in a similar manner to that of Example 1-(2) to give 7-[2-(2-amino-5-bromothiazol-4-yl)-2-methoxyiminoacetamido]-3-(1-methyl-1H-tetrazol-5-ylthiomethyl)-3-cephem-4-carboxylic acid hydrochloride (syn isomer, 660 mg.).

Thus obtained product (450 mg.) was treated with sodium bicarbonate in a similar manner to that of Example 1-(2) to give 7-[2-(2-amino-5-bromothiazol-4-yl)-2-methoxyiminoacetamido]-3-(1-methyl-1H-tetrazol-5-ylthiomethyl)-3-cephem-4-carboxylic acid (syn isomer, 330 mg.).

I.R. (Nujol): νmax: 3400, 3200, 1780, 1680 (broad), 1630 (broad), 1540 cm$^{-1}$.

N.M.R. (DMSO-d$_6$): δppm: 3.52, 3.74 (2H, AB$_q$, J=16 Hz), 3.84 (3H, s), 3.90 (3H, s), 4,16, 4.34 (2H, AB$_q$, J=12 Hz), 5.06 (1H, d, J=4 Hz), 5.72 (1H, d, d, J=4 Hz, 8 Hz), 7.32 (2H, broad s), 9.50 (1H, d, J=8 Hz).

EXAMPLE 4

(1) A solution of 7-amino-3-hydroxymethyl-3-cephem-4-carboxylic acid (2.5 g.) and trimethylsilylacetamide (10.6 g.) in dry ethyl acetate (60 ml.) and a mixture of dimethylformamide (0.75 ml.), phosphoryl chloride (0.88 ml.), 2-(2-formamido-5-bromothiazol-4-yl)-2-methoxyiminoacetic acid (syn isomer, 2.5 g.) and dry ethyl acetate (7.0 ml.) were stirred at −20° to −10° C. for an hour. The reaction mixture was added to aqueous solution (50 ml.) of sodium bicarbonate (3.3 g.), under ice-cooling. Methanol (2 ml.) was added to the mixture and stirred under ice-cooling for 30 minutes. The mixture was washed with ethyl acetate twice. After removing the ethyl acetate, the aqueous solution was adjusted to pH 6.5 with sodium bicarbonate and allowed to stand in a refrigerator. The solution was adjusted to pH 5.0 with 6N-hydrochloric acid and subjected to column chromatography on non-ionic adsorption resin HP-20 (Trademark, manufactured by Mitsubishi Chemical Industries Ltd.), washed with water (200 ml.) and then eluted with 20% isopropyl alcohol (400 ml.). The eluate was evaporated in vacuo. The residue was pulverized with acetone (80 ml.), and the precipitates were collected by filtration and dried to give sodium 7-[2-(2-formamido-5-bromothiazol-4-yl)-2-methoxyiminoacetamido]-3-hydroxymethyl-3-cephem-4-carboxylate (syn isomer, 1.9 g.).

I.R. (Nujol): νmax: 3300 (broad), 1760, 1680 (broad), 1600 (broad), 1550 (broad) cm$^{-1}$.

N.M.R. (D$_2$O): δppm: 3.50–3.73 (2H, broad s), 4.08 (3H, s), 4.32 (2H, s), 5.23 (1H, d, J=4 Hz), 5.87 (1H, d, J=4 Hz), 8.57 (1H, s).

(2) A solution of trichloroacetyl isocyanate (1.32 g.) in dry acetone (5 ml.) was added dropwise to a solution of sodium 7-[2-(2-formamido-5-bromothiazol-4-yl)-2-methoxyiminoacetamido]-3-hydroxymethyl-3-cephem-4-carboxylate (1.9 g.) in dry dimethylformamide at −30° C. and stirred at −40° to −20° C. for 3.5 hrs. Water (20 ml.) was added dropwise to the reaction mixture below −20° C. and the mixture was poured into water (180 ml.). The mixture was adjusted to pH 2 with 6N-hydrochloric acid and extracted with ethyl acetate. The extract was washed with water, dried over magnesium sulfate and evaporated in vacuo. The residue was washed with diethyl ether and dried to give 7-[2-(2-formamido-5-bromothiazol-4-yl)-2-methoxyiminoacetamido]-3-trichloroacetylcarbamoyloxymethyl-3-cephem-4-carboxylic acid (syn isomer, 1.9 g.).

I.R. (Nujol): νmax: 3300, 1790, 1730, 1660 (broad), 1530 (broad) cm$^{-1}$.

N.M.R. (DMSO-d$_6$): δppm: 3.75–3.73 (2H, broad s), 3.95 (3H, s), 4.93–5.10 (2H, broad s), 5.20 (1H, d, J=4 Hz), 5.85 (1H, d, d, J=4 Hz, 8 Hz), 8.53 (1H, s), 9.67 (1H, d, J=8 Hz).

(3) 7-[2-(2-Formamido-5-bromothiazol-4-yl)-2-methoxyiminoacetamido]-3-trichloroacetylcarbamoyloxymethyl-3-cephem-4-carboxylic acid (syn isomer, 1.9 g.) was added to an aqueous solution (80 ml.) of sodium bicarbonate (225 mg.), and adjusted to pH 7.0 with saturated aqueous sodium bicarbonate. Methanol (4 ml.) was added to the solution and stirred at room temperature for 2.5 hrs. The reaction mixture was adjusted to pH 7.5 and washed with ethyl acetate. The aqueous solution was adjusted to pH 2.0 with 6N-hydrochloric acid and extracted with ethyl acetate. The extract was washed with aqueous sodium chloride, dried over magnesium sulfate and evaporated in vacuo. The residue was washed with diethyl ether and dried to give 7-[2-(2-formamido-5-bromothiazol-4-yl)-2-methoxyiminoacetamido]-3-carbamoyloxymethyl-3-cephem-4-carboxylic acid (syn isomer, 0.95 g.).

I.R. (Nujol): νmax: 3300, 1780, 1670 (broad), 1540 cm$^{-1}$.

N.M.R. (DMSO-d$_6$/D$_2$O): δppm: 3.40–3.67 (2H, broad s), 3.93 (3H, s), 4.60, 4.93 (2H, AB$_q$, J=12 Hz), 5.13 (1H, d, J=4 Hz), 5.80 (1H, d, d, J=4 Hz, 8 Hz), 6.53 (2H, s), 8.53 (1H, s), 9.60 (1H, d, J=8 Hz), 12.87 (1H, s).

(4) 7-[2-(2-Formamido-5-bromothiazol-4-yl)-2-methoxyiminoacetamido]-3-carbamoyloxymethyl-3-cephem-4-carboxylic acid (syn isomer, 0.9 g.) was treated with conc. hydrochloric acid (0.34 ml.) in a similar manner to that of Example 1-(2) to give 7-[2-(2-amino-5-bromothiazol-4-yl)-2-methoxyiminoacetamido]-3-carbamoyloxymethyl-3-cephem-4-carboxylic acid hydrochloride (syn isomer, 850 mg.).

Thus obtained product (850 mg.) was treated with sodium bicarbonate in a similar manner to that of Example 1-(2) to give 7-[2-(2-amino-5-bromothiazol-4-yl)-2-methoxyiminoacetamido]-3-carbamoyloxymethyl-3-cephem-4-carboxylic acid (syn isomer, 700 mg.).

I.R. (Nujol): νmax: 3300, 1780, 1710 (broad), 1670 (broad), 1540 cm$^{-1}$.

N.M.R. (DMSO-d$_6$): δppm: 3.30–3.60 (2H, broad s), 3.80 (3H, s), 4.53, 4.87 (2H, AB$_q$, J=12 Hz), 5.07 (1H, d, J=4 Hz), 5.70 (1H, d, d, J=4 Hz, 8 Hz), 6.50 (2H, s), 7.30 (2H, s), 9.43 (1H, d, J=8 Hz).

EXAMPLE 5

(1) A solution of 2-(2-formamido-5-methylthiazol-4-yl)-2-methoxyiminoacetic acid (syn isomer, 1.2 g.), dimethylformamide (0.46 ml.) and phosphoryl chloride (0.54 ml.) in dry ethyl acetate (12 ml.) was added to a solution of 7-amino-3-(1,3,4-thiadiazol-2-ylthiomethyl)-3-cephem-4-carboxylic acid (2.12 g.) and trimethylsilylacetamide (6.7 g.) in dry ethyl acetate (20 ml.) at −10° to −20° C. and stirred at the same temperature for 1.5 hrs. The reaction mixture was washed with water and adjusted to pH 8 with an aqueous solution of sodium bicarbonate. The aqueous layer was separated and adjusted to pH 2 with hydrochloric acid. The precipitates were collected by filtration and dried to give 7-[2-(2-formamido-5-methylthiazol-4-yl)-2-methoxyiminoacetamido]-3-(1,3,4-thiadiazol-2-ylthiomethyl)-3-cephem-4-carboxylic acid (syn isomer, 2.9 g.).

I.R. (Nujol): $\nu$max: 3200, 1765, 1680, 1655, 1535 cm$^{-1}$.

N.M.R. (DMSO-d$_6$): $\delta$ppm: 2.51 (3H, s), 3.56, 3.80 (2H, AB$_q$, J=17 Hz), 3.90 (3H, s), 4.28, 4.55 (2H, AB$_q$, J=13 Hz), 5.13 (1H, d, J=5 Hz), 5.80 (1H, d, d, J=9 Hz, 5 Hz), 8.43 (1H, s), 9.53 (1H, d, J=9 Hz), 9.55 (1H, s).

(2) 7-[2-(2-Formamido-5-methylthiazol-4-yl)-2-methoxyiminoacetamido]-3-(1,3,4-thiadiazol-2-ylthiomethyl)-3-cephem-4-carboxylic acid (syn isomer, 2.4 g.) was treated with conc. hydrochloric acid (1.3 ml.) in a similar manner to that of Example 1-(2) to give 7-[2-(2-amino-5-methylthiazol-4-yl)-2-methoxyiminoacetamido]-3-(1,3,4-thiadiazol-2-ylthiomethyl)-3-cephem-4-carboxylic acid hydrochloride (syn isomer, 2.3 g.).

I.R. (Nujol): $\nu$max: 3230, 3050, 1760, 1705, 1660, 1630, 1585, 1520 cm$^{-1}$.

N.M.R. (DMSO-d$_6$): $\delta$ppm: 2.31 (3H, s), 3.75 (2H, broad s), 4.03 (3H, s), 4.30, 4.64 (2H, AB$_q$, J=14 Hz), 5.17 (1H, d, J=5 Hz), 5.90 (1H, d, J=5 Hz), 9.42 (1H, s).

EXAMPLE 6

(1) A solution of 7-amino-3-(1,3,4-thiadiazol-2-ylthiomethyl)-3-cephem-4-carboxylic acid (4.3 g.) and trimethylsilylacetamide (17.1 g.) in dry ethyl acetate (130 ml.) and a solution of dimethylformamide (0.92 ml.), phosphoryl chloride (1.09 ml.) and 2-(2-formamido-5-chlorothiazol-4-yl)-2-methoxyiminoacetic acid (syn isomer, 2.6 g.) in dry ethyl acetate (27 ml.) were treated in a similar manner to that of Example 1-(1) to give 7-[2-(2-formamido-5-chlorothiazol-4-yl)-2-methoxyiminoacetamido]-3-(1,3,4-thiadiazol-2-ylthiomethyl)-3-cephem-4-carboxylic acid (syn isomer, 5.6 g.).

I.R. (Nujol): $\nu$max: 3300, 3030, 1790, 1690, 1660, 1540 cm$^{-1}$.

N.M.R. (DMSO-d$_6$): $\delta$ppm: 3.63–3.83 (2H, broad s), 3.93 (3H, s), 4.27, 4.63 (2H, AB$_q$, J=12 Hz), 5.17 (1H, d), 5.83 (1H, d, d, J=4 Hz, 8 Hz), 8.57 (1H, s), 9.58 (1H, s), 9.67 (1H, d, J=8 Hz), 12.88 (1H, s).

(2) 7-[2-(2-Formamido-5-chlorothiazol-4-yl)-2-methoxyiminoacetamido]-3-(1,3,4-thiadiazol-2-ylthiomethyl)-3-cephem-4-carboxylic acid (syn isomer, 5.6 g.) was treated with conc. hydrochloric acid (2.4 ml.) in a similar manner to that of Example 1-(2) to give 7-[2-(2-amino-5-chlorothiazol-4-yl)-2-methoxyiminoacetamido]-3-(1,3,4-thiadiazol-2-ylthiomethyl)-3-cephem-4-carboxylic acid hydrochloride (syn isomer, 3.3 g.).

Thus obtained product (3.3 g.) was treated with sodium bicarbonate in a similar manner to that of Example 1-(2) to give 7-[2-(2-amino-5-chlorothiazol-4-yl)-2-methoxyiminoacetamido]-3-(1,3,4-thiadiazol-2-yl-thiomethyl)-3-cephem-4-carboxylic acid (syn isomer, 2.8 g.).

I.R. (Nujol): $\nu$max: 3300, 1780, 1680, 1550 (broad) cm$^{-1}$.

N.M.R. (DMSO-d$_6$): $\delta$ppm: 3.52–3.76 (2H, broad s), 3.86 (3H, s), 4.24, 4.58 (2H, AB$_q$, J=12 Hz), 5.10 (1H, d, J=4 Hz), 5.76 (1H, d, d, J=4 Hz, 8 Hz), 9.54 (1H, s), 9.58 (1H, d, J=8 Hz).

EXAMPLE 7

(1) A solution of 7-amino-3-benzoyloxymethyl-3-cephem-4-carboxylic acid (0.67 g.) and trimethylsilylacetamide (2.1 g.) in dry ethyl acetate (20 ml.) and a solution of dimethylformamide (0.2 ml.), phosphoryl chloride (0.24 ml.) and 2-(2-formamido-5-bromothiazol-4-yl)-2-methoxyiminoacetic acid (syn isomer, 0.62 g.) in dry ethyl acetate (1 ml.) were treated in a similar manner to that of Example 1-(1) to give 7-[2-(2-formamido-5-bromothiazol-4-yl)-2-methoxyiminoacetamido]-3-benzoyloxymethyl-3-cephem-4-carboxylic acid (syn isomer, 430 mg.).

I.R. (Nujol): $\nu$max: 3300, 3030, 1790, 1730, 1690, 1660 cm$^{-1}$.

N.M.R. (DMSO-d$_6$): $\delta$ppm: 3.60–3.83 (2H, broad s), 3.93 (3H, s), 5.17 (1H, d, J=4 Hz), 5.23, 5.93 (2H, AB$_q$, J=12 Hz), 5.85 (1H, d, d, J=4 Hz, 8 Hz), 7.47–8.13 (5H, m), 9.67 (1H, d, J=8 Hz), 12.90 (1H, s).

(2) 7-[2-(2-Formamido-5-bromothiazol-4-yl)-2-methoxyiminoacetamido]-3-benzoyloxymethyl-3-cephem-4-carboxylic acid (syn isomer, 0.58 g.) was treated with conc. hydrochloric acid (0.16 ml.) in a similar manner to that of Example 1-(2) to give 7-[2-(2-amino-5-bromothiazol-4-yl)-2-methoxyiminoacetamido]-3-benzoyloxymethyl-3-cephem-4-carboxylic acid hydrochloride (syn isomer, 0.5 g.).

Thus obtained product (0.5 g.) was suspended in water (15 ml.) and then dissolved by addition of saturated aqueous sodium bicarbonate. The solution was adjusted to pH 5.5 with 1N-hydrochloric acid, subjected to column chromatography on non-ionic adsorption resin HP-20 (Trademark, manufactured by Mitsubishi Chemical Industries Ltd.), and then eluted with 15 to 30% aqueous isopropyl alcohol. The fractions containing the object compound were combined and lyophilized to give sodium 7-[2-(2-amino-5-bromothiazol-4-yl)-2-methoxyiminoacetamido]-3-benzoyloxymethyl-3-cephem-4-carboxylate (syn isomer, 370 mg.).

I.R. (KBr): $\nu$max: 3500, 1770, 1720, 1680, 1620, 1540 cm$^{-1}$.

N.M.R. (DMSO-d$_6$): $\delta$ppm: 3.43–3.70 (2H, broad s), 3.93 (3H, s), 5.07, 5.40 (2H, AB$_q$, J=12 Hz), 5.07 (1H, d, J=4 Hz), 5.67 (1H, d, d, J=4 Hz, 8 Hz), 7.33–8.17 (5H, m), 9.47 (1H, d, J=8 Hz).

EXAMPLE 8

(1) A solution of 4-nitrobenzyl 7-amino-3-cephem-4-carboxylate (3.3 g.), trimethylsilylacetamide (6.4 g.) and bis(trimethylsilyl)acetamide (6.0 g.) in dry ethyl acetate (100 ml.) and a solution of dimethylformamide (0.9 ml.), phosphoryl chloride (1.1 ml.) and 2-(2-formamido-5-bromothiazol-4-yl)-2-methoxyiminoacetic acid (syn isomer, 5.1 g.) in dry ethyl acetate (5 ml.) were treated in a similar manner to that of Example 1-(1) (isopropyl alcohol was used for pulverization instead of diethyl ether) to give 4-nitrobenzyl 7-[2-(2-formamido-5-bromothiazol-4-yl)-2-methoxyiminoacetamido]-3-cephem-4-carboxylate (syn isomer, 2.65 g.).

I.R. (Nujol): νmax: 3300, 1780, 1740, 1690 (broad), 1610, 1520 cm$^{-1}$.

N.M.R. (DMSO-d$_6$): δppm: 3.50–3.83 (2H, broad s), 4.00 (3H, s), 5.20 (1H, d, J=4 Hz), 5.47 (2H, s), 5.98 (1H, d, d, J=4 Hz, 8 Hz), 6.57–6.83 (1H, m), 7.73, 8.30 (4H, AB$_q$, J=8 Hz), 8.57 (1H, s), 9.70 (1H, d, J=8 Hz).

(2) 4-Nitrobenzyl 7-[2-(2-formamido-5-bromothiazol-4-yl)-2-methoxyiminoacetamido]-3-cephem-4-carboxylate (syn isomer, 2.65 g.) was add to a mixture of tetrahydrofuran (110 ml.) and methanol (80 ml.). To the solution was added a suspension of 10% palladium on carbon (1.5 g.) in acetic acid (10 ml.) and the mixture was subjected to catalytic hydrolysis at room temperature under ordinal pressure. The reaction mixture was filtered and washed with tetrahydrofuran. The filtrate and washings were combined and evaporated in vacuo. Ethyl acetate was added to the residue, adjusted to pH 7.5 with saturated aqueous sodium bicarbonate and filtered. The aqueous layer was separated and washed with ethyl acetate. 100 ml. of 20% Isopropyl alcohol in ethyl acetate was added to the aqueous solution and adjusted to pH 2.0 with 6N-hydrochloric acid. The mixture was saturated with sodium chloride and the organic layer was separated. The remaining aqueous layer was extracted with a mixture (100 ml. and 50 ml.) of ethyl acetate and isopropyl alcohol (4:1). The organic layer and the extracts were combined, washed with a small amount of saturated aqueous sodium chloride, dried over magnesium sulfate, treated with activated charcoal and then evaporated in vacuo. The residue was pulverized with diisopropyl ether and the precipitates were collected by filtration, washed with diisopropyl ether and dried to give 7-[2-(2-formamido-5-bromothiazol-4-yl)-2-methoxyiminoacetamido]-3-cephem-4-carboxylic acid (syn isomer, 0.8 g.).

I.R. (Nujol): νmax: 3300, 3050, 1780, 1670, 1550 cm$^{-1}$.

N.M.R. (DMSO-d$_6$): δppm: 3.40–3.64 (2H, broad s), 3.90 (3H, s), 5.04 (1H, d, J=4 Hz), 5.78 (1H, d, d, J=4 Hz, 8 Hz), 6.32–6.50 (1H, broad s), 8.48 (1H, s), 9.60 (1H, d, J=8 Hz).

(3) 7-[2-(2-Formamido-5-bromothiazol-4-yl)-2-methoxyiminoacetamido]-3-cephem-4-carboxylic acid (syn isomer, 0.8 g.) was treated with conc. hydrochloric acid (0.4 ml.) in a similar manner to that of Example 1-(2) to give 7-[2-(2-amino-5-bromothiazol-4-yl)-2-methoxyiminoacetamido]-3-cephem-4-carboxylic acid hydrochloride (syn isomer, 700 mg.).

Thus obtained product (700 mg.) was treated with sodium bicarbonate in a similar manner to that of Example 1-(2) to give 7-[2-(2-amino-5-bromothiazol-4-yl)-2-methoxyiminoacetamido]-3-cephem-4-carboxylic acid (syn isomer, 570 mg.).

I.R. (Nujol): νmax: 3300, 3030, 1780, 1670, 1630, 1540 cm$^{-1}$.

N.M.R. (DMSO-d$_6$): δppm: 3.43–3.70 (2H, broad s), 3.88 (3H, s), 5.10 (1H, d, J=4 Hz), 5.82 (1H, d, d, J=4 Hz, 8 Hz), 6.40–6.63 (1H, m), 7.37 (2H, s), 9.50 (1H, d, J=8 Hz)

EXAMPLE 9

(1) A solution of 7-amino-2-methyl-3-cephem-4-carboxylic acid (1.0 g.) and trimethylsilylacetamide (3.7 g.) in dry ethyl acetate (30 ml.) and a solution of dimethylformamide (0.47 ml.), phosphoryl chloride (0.56 ml.) and 2-(2-formamido-5-bromothiazol-4-yl)-2-methoxyiminoacetic acid (syn isomer, 1.6 g.) in dry ethyl acetate (11.6 ml.) were treated in a similar manner to that of Example 1-(1) to give 7-[2-(2-formamido-5-bromothiazol-4-yl)-2-methoxyiminoacetamido]-2-methyl-3-cephem-4-carboxylic acid (syn isomer, 1.85 g.).

I.R. (Nujol): νmax: 3300, 3030, 1780, 1680, 1540 cm$^{-1}$.

N.M.R. (DMSO-d$_6$): δppm: 1.40 (3H, d, J=8 Hz), 3.80 (1H, m), 3.88 (3H, s), 5.07 (1H, d, J=4 Hz), 5.87 (1H, d,d, J=4 Hz, 8 Hz), 6.55 (1H, d, J=6 Hz), 8.53 (1H, s), 9.60 (1H, d, J=8 Hz), 12.92 (1H, s).

(2) 7-[2-(2-Formamido-5-bromothiazol-4-yl)-2-methoxyiminoacetamido]-2-methyl-3-cephem-4-carboxylic acid (syn isomer, 1.8 g.) was treated with conc. hydrochloric acid (0.89 ml.) in a similar manner to that of Example 1-(2) to give 7-[2-(2-amino-5-bromothiazol-4-yl)-2-methoxyiminoacetamido]-2-methyl-3-cephem-4-carboxylic acid hydrochloride (syn isomer, 1.8 g.).

Thus obtained product (1.8 g.) was treated with sodium bicarbonate in a similar manner to that of Example 1-(2) to give 7-[2-(2-amino-5-bromothiazol-4-yl)-2-methoxyiminoacetamido]-2-methyl-3-cephem-4-carboxylic acid (syn isomer, 1.3 g.).

I.R. (Nujol): νmax: 3300, 1780, 1670, 1630, 1540 cm$^{-1}$.

N.M.R. (DMSO-d$_6$): δppm: 1.43 (3H, d, J=8 Hz), 3.77 (1H, m), 3.87 (3H, s), 5.07 (1H, d, J=4 Hz), 5.83 (1H, d, d, J=4 Hz, 8 Hz), 6.53 (1H, d, J=6 Hz), 9.50 (1H, d, J=8 Hz).

EXAMPLE 10

(1) A solution of 4-nitrobenzyl 7-amino-2-methoxy-3-cephem-4-carboxylate hydrochloride (2.0 g.), trimethylsilylacetamide (2.0 g.) and 2,6-lutidine (0.58 ml.) in dry ethyl acetate (60 ml.) and a solution of dimethylformamide (0.51 ml.), phosphoryl chloride (0.60 ml.) and 2-(2-formamido-5-bromothiazol-4-yl)-2-methoxyiminoacetic acid (syn isomer, 1.7 g.) in dry ethyl acetate (11.7 ml.) were treated in a similar manner to that of Example 1-(1) to give 4-nitrobenzyl 7-[2-(2-formamido-5-bromothiazol-4-yl)-2-methoxyiminoacetamido]-2-methoxy-3-cephem-4-carboxylate (syn isomer, 2.9 g.).

I.R. (Nujol): νmax: 3300, 3050, 1790, 1740, 1670, 1530 cm$^{-1}$.

N.M.R. (DMSO-d$_6$): δppm: 3.45 (3H, s), 4.00 (3H, s), 5.13 (1H, d, J=4 Hz), 5.48 (1H, d, J=6 Hz), 5.50 (2H, s), 6.07 (1H, d, d, J=4 Hz, 8 Hz), 6.65 (1H, d, J=6 Hz), 7.77, 8.30 (4H, AB$_q$, J=8 Hz), 8.57 (1H, s), 9.83 (1H, d, J=8 Hz), 12.93 (1H, s).

(2) A solution of 4-nitrobenzyl 7-[2-(2-formamido-5-bromothiazol-4-yl)-2-methoxyiminoacetamido]-2-methoxy-3-cephem-4-carboxylate (syn isomer, 2.9 g.) in a mixture of tetrahydrofuran (110 ml.) and methanol (80 ml.) was treated in a similar manner to that of Example 8-(2) (diethyl ether was used for pulverization instead of diisopropyl ether) to give 7-[2-(2-formamido-5-bromothiazol-4-yl)-2-methoxyiminoacetamido]-2-methoxy-3-cephem-4-carboxylic acid (syn isomer, 1.2 g.).

I.R. (Nujol): νmax: 3300, 3250, 3050, 1780, 1730, 1670, 1550 cm$^{-1}$.

N.M.R. (DMSO-d$_6$): δppm: 3.40 (3H, s), 3.98 (3H, s), 5.03 (1H, d, J=4 Hz), 5.38 (1H, d, J=6 Hz), 6.00 (1H, d, d, J=4 Hz, 8 Hz), 6.47 (1H, d, J=6 Hz), 8.57 (1H, s), 9.73 (1H, d, J=8 Hz), 12.93 (1H, s).

(3) Conc. hydrochloric acid (0.7 ml.) was added to a solution of 7-[2-(2-formamido-5-bromothiazol-4-yl)-2-methoxyiminoacetamido]-2-methoxy-3-cephem-4-carboxylic acid (syn isomer, 1.4 g.) in methanol (45 ml.) and stirred at room temperature for 2 hrs. and further for 3.5 hrs. under ice-cooling. The reaction mixture was treated with activated charcoal. Water (30 ml.) was added to the solution and adjusted to pH 6.5 with 1N-aqueous sodium hydroxide, and methanol was distilled off. Ethyl acetate was added to the residue and adjusted to pH 2.5 with 1N-hydrochloric acid. The ethyl acetate layer was separated and the aqueous layer was washed with ethyl acetate. The ethyl acetate solution obtained above and the washings were combined, dried over magnesium sulfate, treated with activated charcoal and evaporated in vacuo. The residue was pulverized with diethyl ether, and the precipitates were collected by filtration and dried to give 7-[2-(2-amino-5-bromo-thiazol-4-yl)-2-methoxyiminoacetamido]-2-methoxy-3-cephem-4-carboxylic acid (syn isomer, 1.2 g.).

I.R. (Nujol): νmax: 3400, 3250, 1780, 1660, 1520 cm$^{-1}$.

N.M.R. (DMSO-d$_6$): δppm: 3.30 (3H, s), 3.83 (3H, s), 4.92 (1H, d, J=4 Hz), 5.30 (1H, d, J=6 Hz), 5.87 (1H, d, d, J=4 Hz, 8 Hz), 6.38 (1H, d, J=6 Hz), 9.70 (1H, d, J=8 Hz).

What we claim is:

1. A compound of the formula

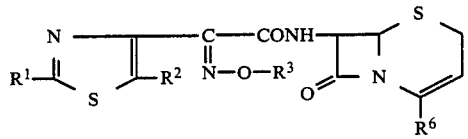

wherein $R^2$ is halogen;

$R^1$ is amino, lower alkanoylamino, or ar(lower)alkoxycarbonylamino;

$R^3$ is lower alkyl; and $R^6$ is carboxy, alkali metal carboxylate, magnesium carboxylate, calcium carboxylate, ar(lower)alkyl carboxylate, or lower alkanoyloxyalkylcarboxylate, or when $R^1$ is amino, a pharmaceutically acceptable acid addition salt thereof.

2. A compound of claim 1, wherein $R^2$ is fluorine, chlorine, or bromine.

3. A compound of claim 1, wherein $R^1$ is amino or a mineral acid addition salt thereof.

4. A compound of claim 1, wherein $R^1$ is lower alkanoylamino or ar(lower)alkoxycarbonylamino.

5. A compound of claim 1, wherein $R^3$ is methyl.

6. A compound of claim 1, wherein $R^6$ is carboxy, sodium carboxylate, potassium carboxylate, magnesium carboxylate, or calcium carboxylate.

7. A compound of claim 1, wherein $R^6$ is ar(lower)alkyl carboxylate or lower alkanoyloxyalkyl carboxylate.

8. A compound of the syn isomer of the formula:

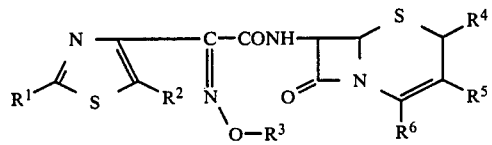

wherein $R^1$ is amino or lower alkanoylamino, $R^2$ is halogen, $R^3$ is lower alkyl, $R^4$ is hydrogen, $R^5$ is hydrogen, and $R^6$ is carboxy or protected carboxy, and its pharmaceutically acceptable salt thereof.

9. 7-[2-(2-amino-5-bromothiazol-4-yl)-2-methoxyiminoacetamido]-3-cephem-4-carboxylic acid (syn isomer).

10. A compound of the syn isomer of the formula:

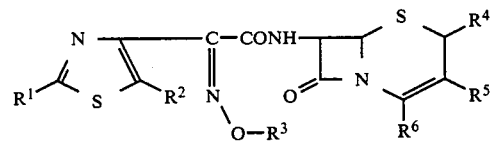

wherein $R^1$ is amino or protected amino, $R^2$ is halogen, $R^3$ is lower alkyl, $R^4$ is hydrogen, $R^5$ is hydrogen, and $R^6$ is carboxy or protected carboxy, and its pharmaceutically acceptable salt thereof.

11. An antibacterial composition comprising a bactericidally effective amount of a compound according to claim 1 and a pharmaceutically acceptable carrier.

12. A composition according to claim 11 in dosage unit form.

* * * * *